United States Patent
Guerret et al.

(10) Patent No.: US 7,126,021 B2
(45) Date of Patent: Oct. 24, 2006

(54) METHOD FOR PREPARING β-PHOSPHORUS NITROXIDE RADICALS

(75) Inventors: Olivier Guerret, Mazerolles (FR); Jean-Luc Couturier, Lyons (FR); Christophe Le Mercier, Caluire et Cuire (FR)

(73) Assignee: Arkema (formerly Atofina), Puteaux (FR)

( * ) Notice: Subject to any disclaimer, the term of this patent is extended or adjusted under 35 U.S.C. 154(b) by 326 days.

(21) Appl. No.: 10/450,128

(22) PCT Filed: Dec. 7, 2001

(86) PCT No.: PCT/FR01/03876

§ 371 (c)(1), (2), (4) Date: Nov. 4, 2003

(87) PCT Pub. No.: WO02/48159

PCT Pub. Date: Jun. 20, 2002

(65) Prior Publication Data

US 2004/0077873 A1 Apr. 22, 2004

(30) Foreign Application Priority Data

Dec. 11, 2000 (FR) .................................. 00 16066

(51) Int. Cl.
*C07F 9/02* (2006.01)
(52) U.S. Cl. .......................... 558/166; 558/73; 568/12; 568/14

(58) Field of Classification Search ............. 558/73, 558/166; 568/12, 14
See application file for complete search history.

(56) References Cited

U.S. PATENT DOCUMENTS

| 6,262,179 | B1 | 7/2001 | Nicol |
| 6,538,141 | B1 | 3/2003 | Gillet et al. |
| 6,624,322 | B1 * | 9/2003 | Gillet et al. ............. 558/166 |
| 6,646,079 | B1 | 11/2003 | Guerret et al. |

FOREIGN PATENT DOCUMENTS

| WO | WO 9624620 | 8/1996 |
| WO | WO 0040526 | 7/2000 |
| WO | WO 0040550 | 7/2000 |

* cited by examiner

*Primary Examiner*—Taofiq Solola
*Assistant Examiner*—Ebenezer Sackey
(74) *Attorney, Agent, or Firm*—Millen, White, Zelano & Branigan, P.C.

(57) ABSTRACT

The present invention relates to a process for the preparation of β-phosphorated nitroxide radicals which consist in preparing, in a first step, an aminophosphonate by reaction of a carbonyl compound, of a primary amine and of a phosphorous compound in the presence of a Lewis acid and then, in a second step, in oxidizing the said crude aminophosphonate using nonhalogenated organic peracids in a water/organic solvent two-phase medium with an aqueous phase buffered at a pH ranging from 5 to 12.

12 Claims, No Drawings

METHOD FOR PREPARING β-PHOSPHORUS NITROXIDE RADICALS

A subject-matter of the present invention is a process for the preparation of β-phosphorated nitroxide radicals of formula:

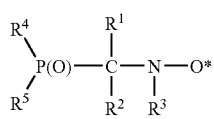
(I)

in which $R^1$, $R^2$, $R^3$, $R^4$ and $R^5$ will be defined subsequently. These compounds are used in particular as regulators of radical polymerization.

These compounds can be obtained in particular by the oxidation of N-alkylaminophosphonates of formula:

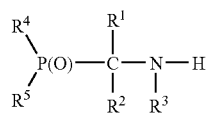
(II)

The N-alkylaminophosphonates (II) can be obtained in a known way by reacting a carbonyl compound $R^1R^2C(O)$, a primary amine $R^3NH_2$ and a phosphorus compound $HP(O)R^4R^5$ having a mobile hydrogen according to a Mannich-type reaction:

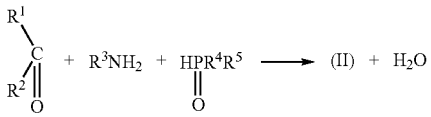

A process is disclosed in international patent application WO 96/24620 which consists in reacting, in a first stage, a carbonyl compound $R^1R^2C(O)$ with a primary amine $R^3NH_2$ according to a carbonyl compound/primary amine molar ratio substantially equal to 1 and then, in a second stage, in adding, to the compound obtained in the first stage, a phosphorus compound $HP(O)R^4R^5$ according to a phosphorus compound/product obtained in the first stage molar ratio ranging from 1.5 to 2.5, indeed even more. There are several disadvantages to this way of proceeding.

Thus, the water formed in the first stage during the reaction of the carbonyl compound with the primary amine which results in the formation of an imine according to the scheme:

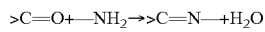
>C=O+—NH₂→>C=N—+H₂O is not removed before the addition of the phosphorus compound, which may be of such a nature as to result in a possible hydrolysis of the said phosphorus compound, in particular when the latter is a phosphite.

In addition, the use of a very large excess of phosphorus compound (150% to 250%, indeed even more) with respect to the compound obtained in the first stage (imine) is prohibitory for an industrial process.

Furthermore, this excess, in addition to the fact of the difficulties in removing it, is of such a nature as to generate numerous impurities by reaction with, in particular, the unconverted carbonyl compound to result in hydroxyphosphonates (>C(OH)—P(O)<) in the case where the phosphorus compound used is a phosphite. This excess of phosphorus compound can also result in the formation of heavy products resulting from the reaction between (II), the carbonyl compound and the excess phosphorus compound $HP(O)R^4R^5$.

All these impurities liable to be present in the crude product (II) make the purification of the N-alkylaminophosphonate (II) difficult and consequently render its subsequent use difficult.

In order to overcome these disadvantages, the Applicant Company has synthesized the aminophosphonate (II) by reaction of a carbonyl compound $R^1R^2C(O)$, of a primary amine $R^3NH_2$ and of a phosphorous compound $HP(O)R^4R^5$, the following stages being carried out:

a) a carbonyl compound $R^1R^2C(O)$ is reacted with a primary amine $R^3NH_2$ according to an $R^1R^2C(O)/R^3NH_2$ molar ratio of between 0.8 and 1.5 and preferably between 0.9 and 1.1 at a temperature of between 0° C. and 120° C. and a pressure ranging from 1 to 10 bar; then the water formed is removed from the reaction medium;

b) the compound obtained in a) is reacted with a phosphorus compound $HP(O)R^4R^5$ used according to an $HP(O)R^4R^5$/compound a) molar ratio at most equal to 1.5 and preferably of between 1 and 1.5 at a temperature of between 0° C. and 120° C.;

c) an acidic treatment of the reaction medium obtained in b) is carried out, an organic solvent is subsequently added, separation by settling is carried out, the aqueous phase is recovered and then a basic treatment of the said aqueous phase is carried out;

d) the aminophosphonate is extracted by means of an organic solvent identical to that used previously in c);

e) the said solvent is then completely removed and the said aminophosphonate (II) is isolated and is oxidized to β-phosphorated nitroxide according to the stages $a^1$), $b^1$) and $c^1$) described below.

Although it is possible, by operating in this way, to overcome some disadvantages of the prior art, it is nevertheless a fact that the reaction between the phosphite and the imine—stage b)—is lengthy (several hours) and that the aminophosphonate II, although devoid of heavy impurities, is obtained at the price of a tedious acid/base purification and extraction treatment in a solvent medium which is burdensome to the overall process for obtaining the β-phosphorated nitroxide (I), which nitroxide is obtained by oxidation of the said aminophosphonate (II) according to a process disclosed in Application FR 2 788 270, incorporated in the present document by reference.

This process consists in oxidizing the aminophosphonate (II) by carrying out the following stages:

$a^1$) the aminophosphonate (II) obtained in e) is dissolved in a water-immiscible organic solvent, then;

$b^1$) subsequently, an amount of non-halogenated organic peracid, according to a peracid/aminophosphonate (II) molar ratio ranging from 1.5 to 2.5, and a sufficient amount of a basic aqueous solution of an alkali metal carbonate or hydrogencarbonate or of an alkaline earth metal carbonate or hydrogencarbonate or alternatively of an ammonia solution to produce a pH ranging from 5 to 12 and preferably ranging from 6 to 9 are simultaneously added with vigorous stirring, at a temperature of between −10° C. and +40° C. and preferably of between −5° C. and +30° C., to the medium thus obtained, until the aminophosphonate (II) has been completely converted;

c¹) the organic phase is then recovered by simple separation by settling and the β-phosphorated nitroxide is isolated by evaporation of the organic solvent under reduced pressure.

This oxidation process makes it possible to obtain a β-phosphorated nitroxide with a purity satisfactory for subsequent use thereof but the overall productive output of the process is lowered because the preparation of the aminophosphonate II is lengthy and requires, in order to have a purity which is sufficient to be oxidized, an expensive purification and isolation treatment.

The Applicant Company has now found that it can rapidly obtain an aminophosphonate while avoiding the stages c) and d) of the acid/base treatment in a solvent medium and the extraction stage e), this being achieved while operating with a phosphite/imine molar ratio substantially equal to 1 and while carrying out stage b) in the presence of a Lewis acid.

A subject-matter of the present invention is thus a process for the manufacture of compounds of general formula:

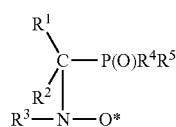

(I)

in which $R^1$ and $R^2$, which are identical or different, represent a hydrogen atom, a linear, branched or cyclic alkyl radical having a number of carbon atoms ranging from 1 to 10, an aryl radical, or an aralkyl radical having a number of carbon atoms ranging from 1 to 10, or else $R^1$ and $R^2$ are connected to one another so as to form a ring which includes the carbon atom carrying the said $R^1$ and $R^2$ radicals, the said ring having a number of carbon atoms, including the carbon carrying the $R^1$ and $R^2$ radicals, ranging from 3 to 8; $R^3$ represents a linear or branched and saturated or unsaturated hydrocarbonaceous radical which can comprise at least one ring, the said radical having a number of carbon atoms ranging from 1 to 30; and $R^4$ and $R^5$, which are identical or different, represent a linear or branched alkyl radical having a number of carbon atoms ranging from 1 to 20 or a cycloalkyl, aryl, alkoxyl, aryloxyl, aralkyloxyl, perfluoroalkyl, aralkyl, dialkyl- or diarylamino, alkylarylamino or thioalkyl radical, or else $R^4$ and $R^5$ are connected to one another so as to form a ring which includes the phosphorus atom, the said heterocycle having a number of carbon atoms ranging from 2 to 4 and being able in addition to comprise one or more oxygen, sulphur or nitrogen atoms;

the said process consisting in oxidizing an aminophosphonate of formula

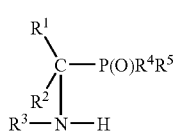

(II)

in a solvent medium using a nonhalogenated organic peracid in a water/solvent two-phase medium with an aqueous phase buffered at a pH ranging from 5 to 12; the said aminophosphonate being obtained by reaction of a carbonyl compound $R^1R^2C(O)$, of a primary amine $R^3NH_2$ and of a phosphorus compound $HP(O)R^4R^5$, $R^1$, $R^2$, $R^3$, $R^4$ and $R^5$ having the meanings given above, by carrying out the following (successive) stages:

a) a carbonyl compound $R^1R^2C(O)$ is reacted with a primary amine $R^3NH_2$ according to an $R_1R^2C(O)/R^3NH_2$ molar ratio of between 0.8 and 1.5 and preferably between 0.9 and 1.1 at a temperature of between 0° C. and 120° C. and a pressure ranging from 1 to 10 bar; then the water formed is removed from the reaction medium; and b) the compound obtained in a) is reacted with a phosphorus compound $HP(O)R^4R^5$;

the said process being characterized in that stage b) is carried out in the presence of a Lewis acid using an $HP(O)R^4R^5/$ compound obtained in stage a) molar ratio substantially equal to 1 at a temperature at most equal to 100° C. and in that the medium obtained in b) is subjected directly and without purification to an oxidation reaction carried out according to the conditions mentioned above.

The purity of the β-phosphorated nitroxide obtained can be improved by flash distillation under reduced pressure or by low temperature crystallization.

According to the present invention, the Lewis acid is chosen from $BF_3$ and its complexes with ethers, such as diethyl ether or tetrahydrofuran; lanthanide trifluorates, such as ytterbium trifluoromethane-sulphonate $(CF_3SO_3)_3Yb$; $SnCl_4$, $SnCl_2$ or $ZnCl_2$.

Preferably, boron trifluoride diethyl ether $(CH_3CH_2)_2O.BF_3$ will be used.

The Lewis acid is used in a molar amount at most equal to 20% with respect to the imine obtained in stage a) and preferably in a molar amount of between 5% and 15%.

Mention will be made, by way of illustration of carbonyl compounds $R^1R^2C(O)$ which can be used according to the present invention, of trimethylacetaldehyde (pivalaldehyde), isobutyraldehyde, cyclohexanecarboxaldehyde, diethyl ketone, dibutyl ketone, methyl ethyl ketone, cyclohexanone, 4-tert-butylcyclohexanone or α-tetralone.

Mention will be made, by way of illustration of primary amines $R^3$—$NH_2$ which can be used according to the present invention, of methylamine, ethylamine, propylamine, isopropylamine, tert-butylamine, diphenylmethylamine, triphenylmethylamine, aniline, α-naphthylamine, benzylamine, 1-phenylethylamine, cyclohexylamine or cyclopentylamine.

Use will preferably be made of tert-butylamine, isopropylamine, diphenylmethylamine, 1-phenylethylamine or cyclohexylamine.

The reaction between the carbonyl compound $R^1R^2C(O)$ and the amine $R^3NH_2$ (stage a) is carried out with vigorous stirring at a temperature of between 0° C. and 120° C. and preferably at a temperature of between 0° C. and 60° C. The reaction is generally carried out at a pressure of between 1 bar and 10 bar, preferably at atmospheric pressure, and under an inert gas atmosphere, such as nitrogen or argon. The reaction time can vary within wide limits. It depends on the reactivity of the amine employed. The complete conversion of the carbonyl compound $R^1R^2C(O)$ can be confirmed by chromatographic (GC) analysis.

On completion of the reaction, stirring is halted and the reaction medium is allowed to separate by settling. Separation by settling is generally rapid. The aqueous phase, consisting virtually entirely of the water formed during the reaction between the carbonyl compound and the primary amine which results in the imine (III), according to the scheme:

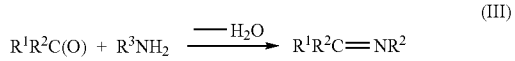

$$R^1R^2C(O) + R^3NH_2 \xrightarrow{-H_2O} R^1R^2C=NR^2 \quad (III)$$

is subsequently removed.

The removal of the water can be completed by the addition of a dehydrating agent, such as a molecular sieve, to the phase which has been separated by settling or alternatively azeotropic distillation can be carried out.

The imine (III) obtained in stage a) is reacted with a compound $HP(O)R^4R^5$ (stage b)) in the presence of a Lewis acid.

Mention will be made, by way of illustration of phosphorus compounds $HP(O)R^4R^5$ which can be used according to the present invention, of dimethyl phosphite, diethyl phosphite, di(n-propyl) phosphite, dibenzyl phosphite, diisopropyl phosphite, di(n-dodecyl) phosphite, diphenylphosphine oxide or dibenzylphosphine oxide.

The phosphorous compound $HP(O)R^4R^5$ is added to the imine (III) obtained in stage a) with vigorous stirring at a temperature at most equal to 100° C. and preferably at a temperature of between 40° C. and 80° C. As in stage a), the reaction is carried out under an inert gas atmosphere and preferably at atmospheric pressure. On completion of the addition, the Lewis acid is slowly added.

As the addition of the Lewis acid is exothermic, the temperature is allowed to rise to at most 100° C. and preferably between 40° C. and 80° C. On completion of the addition, the reaction medium is kept stirred at most 1 hour at a temperature reached at the end of the addition of the Lewis acid.

The phosphorous compound $HP(O)R^4R^5$ is used, with respect to the imine obtained in stage a), according to a phosphorous compound/imine (III) molar ratio substantially equal to 1.

The reaction medium obtained in stage b) is subsequently subjected directly to an oxidation reaction according to stages $a^1$) to $c^1$) described above.

Mention will be made, by way of illustration of organic solvents which can be used according to the present invention in stages $a^1$) to $c^1$), of aliphatic hydrocarbons, such as pentane, heptane or cyclohexane; chlorinated solvents, such as $CH_2Cl_2$; esters of aliphatic acids, such as ethyl acetate or ethyl propionate, or a mixture of at least two of the above-mentioned solvents.

Mention will be made, by way of illustration of nonhalogenated organic peracids which can be used according to the present invention, of peracetic acid, perpropionic acid or perbutanoic acid.

The compounds (I) can be identified by elemental analysis, HPLC, IR and EPR.

The compounds (II) obtained according to the invention can be identified by proton, $^{13}C$ and $^{31}P$ NMR, by IR and by elemental analysis.

The compounds obtained according to the process of the present invention have a sufficient purity to be used as regulators of radical polymerizations.

The process according to the present invention is fast and exhibits the advantage of not using solvent during the synthesis of the aminophosphonate and not having to purify the said aminophosphonate, which reduces the amount of effluents to be treated. This results in reduced handling operations, allowing the productive output of the process to be increased.

The process according to the present invention also exhibits the advantage of resulting in high yields of β-phosphorated nitroxide radicals.

The example which follows illustrates the invention.

EXAMPLE

Preparation of N-tert-butyl-1-diethylphosphono-2,2-dimethylpropyl Nitroxide (Hereinafter Nitroxide) by Oxidation of Diethyl 2,2-dimethyl-1-(1,1-dimethylethylamino)propylphosphonate (Hereinafter Aminophosphonate)

The reaction is carried out under a nitrogen atmosphere in a 2 1 jacketed SVL reactor equipped with a pressure-equalizer dropping funnel, a reflux condenser exiting into a bubbler, a nitrogen inlet, a mechanical (anchor) stirrer and a temperature probe.

100 g of pivaldehyde (1.16 mol) are charged to the reactor purged with nitrogen. 84.9 g of tert-butylamine (1.16 mol) are charged to the dropping funnel. The tert-butylamine is run in dropwise at ambient temperature. After the tert-butylamine has finished being run in, the mixture is heated to 35° C. and is allowed to react for 2 hours. The mixture is then cooled and the aqueous phase formed is removed.

176.2 g of diethyl phosphite (1.28 mol) are subsequently run in dropwise at 40° C. and then 16.5 g of $(CH_3CH_2)_2O \cdot BF_3$ complex (0.116 mol) are run in dropwise. The temperature is allowed to rise to 60° C. After the complex has finished being run in, the mixture is allowed to react for 1 hour at 60° C.

356 g of crude aminophosphonate are obtained in the form of a colourless liquid. The purity, determined by HPLC, is 80% (yield=90%). The crude reaction product is used as is for the oxidation reaction.

395.5 g of 40% peracetic acid (2.08 mol) are charged to the reactor. 350 g of dichloromethane and 350 g of water are added. The reaction medium is neutralized to pH=7.2 by addition of 35% $K_2CO_3$. While maintaining the temperature at 20–25° C., the 356 g of crude 80% aminophosphonate (1.04 mol) obtained above are run in dropwise while maintaining the pH at 7.2 by addition of $K_2CO_3$. After the aminophosphonate has been run in, the mixture is allowed to react for 1 h at ambient temperature while continuing to maintain the pH at 7.2. At the end of the reaction, the pH is brought to 8 by addition of 35% $K_2CO_3$. Separation by settling is allowed to take place. The aqueous phase is removed. The organic phase is washed with water. The solvent is evaporated under vacuum to give 263 g of nitroxide, existing in the form of an orange liquid. The purity, determined by HPLC, is 85% (0.76 mol). The overall yield is 66%.

What is claimed is:

1. Process for the manufacture of compounds of general formula:

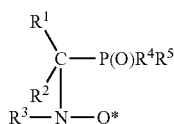

(I)

in which $R^1$ and $R^2$, which are identical or different, represent a hydrogen atom, a linear, branched or cyclic alkyl radical having a number of carbon atoms ranging from 1 to 10, an aryl radical, or an aralkyl radical having a number of carbon atoms ranging from 1 to 10, or else $R^1$ and $R^2$ are connected to one another so as to form a ring which includes the carbon atom carrying the said $R^1$ and $R^2$ radicals, the said ring having a number of carbon atoms, including the carbon carrying the $R^1$ and $R^2$ radicals, ranging from 3 to 8; $R^3$ represents a linear or branched and saturated or unsaturated hydrocarbonaceous radical which can comprise at least one ring, the said radical having a number of carbon atoms ranging from 1 to 30; and $R^4$ and $R^5$, which are identical or different, represent a linear or branched alkyl radical having a number of carbon atoms ranging from 1 to 20 or a cycloalkyl, aryl, alkoxyl, aryloxyl, aralkyloxyl, perfluoroalkyl, aralkyl, dialkyl- or diarylamino, alkylarylamino or thioalkyl radical, or else $R^4$ and $R^5$ are connected to one another so as to form a ring which includes the phosphorus atom, the said heterocycle having a number of carbon atoms ranging from 2 to 4 and being able in addition to comprise one or more oxygen, sulphur or nitrogen atoms;

the said process consisting in oxidizing an aminophosphonate of formula

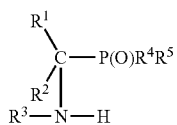

(II)

in a solvent medium using a nonhalogenated organic peracid in a water/solvent two-phase medium with an aqueous phase buffered at a pH ranging from 5 to 12; the said aminophosphonate being obtained by reaction of a carbonyl compound $R^1R^2C(O)$, of a primary amine $R^3NH_2$ and of a phosphorus compound $HP(O)R^4R^5$, $R^1$, $R^2$, $R^3$, $R^4$ and $R^5$ having the meanings given above, by carrying out the following (successive) stages:

a) a carbonyl compound $R^1R^2C(O)$ is reacted with a primary amine $R^3NH_2$ according to an $R^1R^2C(O)/R^3NH_2$ molar ratio of between 0.8 and 1.5 and preferably of between 0.9 and 1.1 at a temperature of between 0° C. and 120° C. and a pressure ranging from 1 to 10 bar; then the water formed is removed from the reaction medium; and b) the compound obtained in a) is reacted with a phosphorus compound $HP(O)R^4R^5$;

the said process being characterized in that stage b) is carried out in the presence of a Lewis acid using an $HP(O)R^4R^5$/compound obtained in stage a) molar ratio substantially equal to 1 at a temperature at most equal to 100° C. and in that the medium obtained in b) is subjected directly and without purification to an oxidation reaction carried out according to the conditions mentioned above.

2. Process according to claim 1, characterized in that the Lewis acid is chosen from $BF_3$, its complexes with diethyl ether or tetrahydrofuran; lanthanide trifluorates, $SnCl_4$, $SnCl_2$ or $ZnCl_2$.

3. Process according to claim 2, characterized in that the Lewis acid is boron trifluoride diethyl ether $(CH_3CH_2)_2O$ $BF_3$.

4. Process according to claim 1, characterized in that the Lewis acid is used in a molar amount at most equal to 20% with respect to the imine obtained in stage a).

5. Process according to claim 4, characterized in that the Lewis acid is used in a molar amount of between 5% and 15%.

6. Process according to claim 1, characterized in that the amine $R^3NH_2$ is tert-butylamine, isopropylamine, diphenylmethylamine, 1-phenylethylamine or cyclohexylamine.

7. Process according to claim 6, characterized in that the amine $R^3NH_2$ is tert-butylamine.

8. Process according to claim 1, characterized in that the phosphorus derivative $HP(O)R^4R^5$ is dimethyl phosphite, diethyl phosphite, di(n-propyl) phosphite, diisopropyl phosphite or dibenzyl phosphite.

9. Process according to claim 8, characterized in that the phosphorus derivative $HP(O)R^4R^5$ is diethyl phosphite.

10. Process according to claim 1, characterized in that the carbonyl compound $R^1R^2C(O)$ is pivalaldehyde, isobutyraldehyde, cyclohexanecarbox-aldehyde or cyclohexanone.

11. Process according to claim 10, characterized in that the carbonyl compound $R^1R^2C(O)$ is pivalaldehyde.

12. Process according to claim 1, characterized in that the nonhalogenated organic peracid is peracetic acid or perpropionic acid.

\* \* \* \* \*

UNITED STATES PATENT AND TRADEMARK OFFICE
CERTIFICATE OF CORRECTION

PATENT NO. : 7,126,021 B2  Page 1 of 1
APPLICATION NO. : 10/450128
DATED : October 24, 2006
INVENTOR(S) : Olivier Guerret It is certified that error appears in the above-identified patent and that said Letters Patent is hereby corrected as shown below:

On the Title page, Inventors: line 2, reads "Lyons" should read -- Lyon --
Column 8, line 2, reads "$R_1R^2C(O)/$" should read -- $R^1R^2C(O)/$ --
Column 8, line 22-23, reads "$(CH_3CH_2)_2OBF_3$." should read -- $(CH_3CH_2)_2O\text{-}BF_3$. --

Signed and Sealed this

Eleventh Day of November, 2008

JON W. DUDAS
*Director of the United States Patent and Trademark Office*